United States Patent
Ledger et al.

(10) Patent No.: US 10,513,681 B2
(45) Date of Patent: Dec. 24, 2019

(54) PGPR COMPOSITIONS AND METHODS FOR IMPROVED CULTIVATION OF TOMATO AND POTATO SPECIES

(71) Applicant: UNIVERSIDAD ADOLFO IBANEZ, Santiago (CL)

(72) Inventors: Thomas Ledger, Santiago (CL); Maria Josefina Poupin, Santiago (CL); Tania Timmermann, Santiago (CL); Macarena Stuardo, Santiago (CL); Bernardo Gonzalez, Santiago (CL); Cedric Little, Vina del Mar (CL)

(73) Assignee: Universidad Adolfo Ibanez, Santiago (CL)

( * ) Notice: Subject to any disclaimer, the term of this patent is extended or adjusted under 35 U.S.C. 154(b) by 0 days.

(21) Appl. No.: 15/115,539

(22) PCT Filed: May 6, 2016

(86) PCT No.: PCT/IB2016/000682
§ 371 (c)(1),
(2) Date: Jul. 29, 2016

(87) PCT Pub. No.: WO2016/181216
PCT Pub. Date: Nov. 17, 2016

(65) Prior Publication Data
US 2018/0044627 A1 Feb. 15, 2018

Related U.S. Application Data

(60) Provisional application No. 62/159,055, filed on May 8, 2015.

(51) Int. Cl.

| | |
|---|---|
| *A01N 25/00* | (2006.01) |
| *A01N 63/02* | (2006.01) |
| *A01N 65/42* | (2009.01) |
| *C12N 1/20* | (2006.01) |
| *A01C 1/06* | (2006.01) |
| *C05F 11/08* | (2006.01) |

(52) U.S. Cl.
CPC ............ *C12N 1/20* (2013.01); *A01C 1/06* (2013.01); *A01N 63/02* (2013.01); *A01N 65/42* (2013.01); *C05F 11/08* (2013.01); *A01N 25/00* (2013.01)

(58) Field of Classification Search
None
See application file for complete search history.

(56) References Cited

U.S. PATENT DOCUMENTS

| | | |
|---|---|---|
| 5,697,186 A | 12/1997 | Neyra et al. |
| 6,524,998 B1 | 2/2003 | Kloepper et al. |
| 2011/0165618 A1 | 7/2011 | Voigt et al. |
| 2015/0020239 A1 | 1/2015 | von Maltzahn et al. |

OTHER PUBLICATIONS

Fuentes-Ramirez et al. "Chapter 5: Bacterial Biofertilizers," PGPR: Biocontrol and Biofertilization, ZA Siddiqui (ed.); pp. 143-172 (Dec. 31, 2005).
Govindarajan et al. "Improved Yield of Micropropagated Sugarcane Following Inoculation by Endophytic Burkholderia Vietnamiensis," Plant and Soil, 208:239-252 (Feb. 1, 2006).
Govindarajan et al. "Effects of the Inoculation of Burkholderia vietnamensis and Related Endophytic Diazotrophic Bacteria on Grain Yield of Rice," Microbial Ecology, 55:21-37 (Jan. 1, 2008).
International Search Report for PCT/IB2016/000682.
Written Opinion of the International Searching Authority for PCT/IB2016/000682.
Bhattacharyya et al., "Plant growth-promoting rhizobacteria (PGPR): emergence in agriculture," World J Microbiol Biotechnol 28:1327-1350 (2012).
Lucy et al., "Applications of free living plant growth-promoting rhizobacteria," Antonie van Leeuwenhoek 86:1-25 (2004).
Babalola, O.O., "Beneficial bacteria of agricultural importance," Biotechnol Left, 32:1559-1570 (2010).
Poupin et al., "Effects of the Plant Growth-Promoting Bacterium Burkholderia phytofirmans PsJN throughout the Life Cycle of *Arabidopsis thaliana*," PLoS ONE 8(7):e69435 (2013).
Zuniga et al., "Quorum Sensing and Indole-3-Acetic Acid Degradation Play a Role in Colonization and Plant Growth Promotion of *Arabidopsis thaliana* by Burkholderia phytofirmans PsJN," MPMI 26(5):546-553 (2013).
Katupitiya et al., "A Mutant of Azospirillum brasilense Sp7 Impaired in Flocculation with a Modified Colonization Pattern and Superior Nitrogen Fixation in Association with Wheat," Appl Environ Microbiol. 61(5):1987-1995 (1995).
Ravikumar et al., "Population dynamics of free living, nitrogen fixing bacteria Azospirillum in Manakkudi mangrove ecosystem, India," J. Environ. Biol. 33:597-602 (2012).
Lugtenberg et al., "Plant-Growth-Promoting Rhizobacteria," Annu. Rev. Microbial. 63:541-56 (2009).
Vacheron et al. "Plant growth-promoting rhizobacteria and root system functioning," Front Plant Sci. 4:356 (2013).
Vejan et al., "Role of Plant Growth Promoting Rhizobacteria in Agricultural Sustainability—A Review," Molecules 21:573 (2016).
Moulin et al., "Complete Genome sequence of Burkholderia phymatum STM815T, a broad host range and efficient nitrogen-fixing symbiont of Mimosa species," Standards in Genomic Sciences 9:763-774 (2014).
Vandamme et al., "*Burkholderia tuberum* sp. nov. and *Burkholderia phymatum* sp. nov., nodulate the roots of tropical legumes," Syst Appl Microbiol. 25(4):507-12 (2002).

*Primary Examiner* — Alton N Pryor
(74) *Attorney, Agent, or Firm* — McDonnell Boehnen Hulbert & Berghoff LLP

(57) ABSTRACT

The disclosure provides methods and compositions to improve the nutritional conditions, such as reducing the use of fertilizers applied during the growing season, and tolerance to fungal pathogens in tomato and potato plants.

16 Claims, 6 Drawing Sheets

A

B

PGPR COMPOSITIONS AND METHODS FOR IMPROVED CULTIVATION OF TOMATO AND POTATO SPECIES

This application is a U.S. National Phase of International Application No. PCT/IB2016/000682 filed on May 6, 2016, which claims the benefit of U.S. Provisional Application No. 62/159,055, filed May 8, 2015, the disclosures of which are incorporated herein by reference in their entirety.

BACKGROUND OF THE INVENTION

Field of the Invention

The disclosure provides methods and compositions to improve the nutritional conditions, such as reducing the use of fertilizers applied during the growing season, and tolerance to fungal pathogens in tomato and potato plants.

Description of the Related Art

Conventional farming methods use fertilizers and pesticides to improve crop yields. Chemical fertilizers, in particular, are applied in increasing amounts in order to provide required nutrients to plants. These fertilizers have acidified the soil and deposited high levels of heavy metals and salts. Overuse of fertilizers and pesticides results in an imbalance of essential nutrients in the amended soils, eventually rendering the land unsuitable for farming. Irrigation and rainwater leach applied fertilizers and pesticides into waterways, causing eutrophication of lakes, rivers and other local water sources, contributing substantially to water pollution and creating non-drinkable or toxic water sources.

Plant-associated microorganisms, such as are root-associated bacteria, have been extensively examined for their roles in the biological approaches for improving crop production. Plant growth-promoting rhizobacteria (PGPR) are a subset of total rhizosphere bacteria and are crucial for soil fertility (Lugtenberg & Kamilova, (2009) "Plant Growth Promoting Rhizobacteria" Annu Rev Microbiol, vol. 63: 541-56). PGPR can colonize the rhizosphere or internal tissues of many plant species, and have the potential to induce positive effects such as increased plant growth, reduced susceptibility to diseases (caused by fungi, bacteria, viruses and nematodes) and improved tolerance to abiotic stresses. When such beneficial effects have been observed, different mechanisms have been proposed to explain rhizobacterial growth promotion: the ability to fix atmospheric nitrogen; solubilization of inorganic nutrients that are rate-limiting for plant growth; stimulation of nutrient delivery and uptake by plant roots; the modulation of plant regulatory mechanisms through the production of hormones such as auxin, gibberellins and cytokinins; the reduction of plant ethylene levels; or the production of other compounds that influence plant development (Vacheron et al., (2013) "Plant growth-promoting rhizobacteria and root system functioning". Front Plant Sci. 4:356).

SUMMARY OF THE INVENTION

While the mechanisms of rhizobacteria-mediated plant growth promotion have not been completely identified, growth-promoting rhizobacteria (PGPR) offer an opportunity to replace the chemical fertilizers and pesticides that have numerous negative side-effects on soil and waterways. The inventors have found that inoculation of plants with a properly designed combination of bacteria providing different, but complementary, PGPR functions, results in a more effective growth promotion than inoculation with one single bacterium, when a specific environmental limitation is encountered, such as lack of available nitrogen. For example, certain *Burkholderia* species, like *B. phymatum*, have been shown to be able to fix nitrogen within root tissue (Moulin et al., (2014) "Complete Genome sequence of *Burkholderia phymatum* STM815(T), a broad host range and efficient nitrogen-fixing symbiont of *Mimosa* species. Stand Genomic Sci. 9(3):763-74), while others, like *B. phytofirmans*, lack nitrogen fixation functions, but possess the ability to regulate plant signalling pathways involved in growth and development (Poupin et al., (2013) "Effects of the Plant Growth Promoting Bacterium *Burkholderia phytofirmans* PsJN throughout the Life-Cycle of *Arabidopsis thaliana*" PLOS ONE, Vol. 8(7), e69435). *Azospirillum* strains like *A. brasilense*, on the other hand, have also been characterized as nitrogen fixers, but they exert this function as free-living component of rhizosphere soil microbiota (Ravikumar et al., (2012) "Population dynamics of free living, nitrogen fixing bacteria *Azospirillum* in Manakkudi mangrove ecosystem", India. J Environ Biol. 33(3):597-602). Thus, the method of the disclosure improves the inoculation of potato and tomato plants with growth-promoting rhizobacteria (PGPR). In a broad aspect, the methods of the disclosure provide improvements in growth and yield of the plants, and also reduce fungal infections of these plants. An added benefit of the methods of the disclosure is that treated tomato and/or potato plants require less, for example about 50% less, of the traditional fertilization application compared to untreated tomato and/or potato plants.

In one aspect, the disclosure provides plant cultivation compositions comprising a) a bacterial species mixture comprising bacteria belonging to *Burkholderia* genus and/or *Azospirillum* genus; and b) a suspension medium.

In another aspect, the disclosure provides plant cultivation compositions comprising a) a bacterial species mixture comprising *Burkholderia phytofirmans*; and b) a suspension medium.

In another aspect, the disclosure provides plant cultivation compositions comprising a) a bacterial species mixture comprising *Burkholderia phymatum*; and b) a suspension medium.

In another aspect, the disclosure provides plant cultivation compositions comprising a) a bacterial species mixture comprising one or more of *Burkholderia phymatum*, and *Azospirillum brasilense*; and b) a suspension medium.

In one aspect, the disclosure provides plant cultivation compositions comprising a) a bacterial species mixture comprising *Burkholderia phytofirmans*, *Burkholderia phymatum*, and *Azospirillum brasilense*; and b) a suspension medium.

In another aspect, the disclosure provides methods for promoting tomato or potato growth, comprising applying an effective amount of a plant cultivation composition of the disclosure to tomato seed beds, tomato plantlet beds, or potato tuber seeds. Additional aspect of the disclosure provides methods for promoting tomato or potato growth, comprising applying an effective amount of a plant cultivation composition of the disclosure to tomato seed, tomato plantlet, or potato tuber seeds to obtain treated seed or tuber, and sowing the treated seed or tuber.

In another aspect, the disclosure provides methods to reducing fungal infections, comprising applying an effective amount of a plant cultivation composition of the disclosure to tomato seed beds, tomato plantlet beds, or potato tuber seeds to obtain treated seed, plantlet or tuber, and sowing the treated seed or tuber.

DETAILED DESCRIPTION OF THE INVENTION

Figure 1:
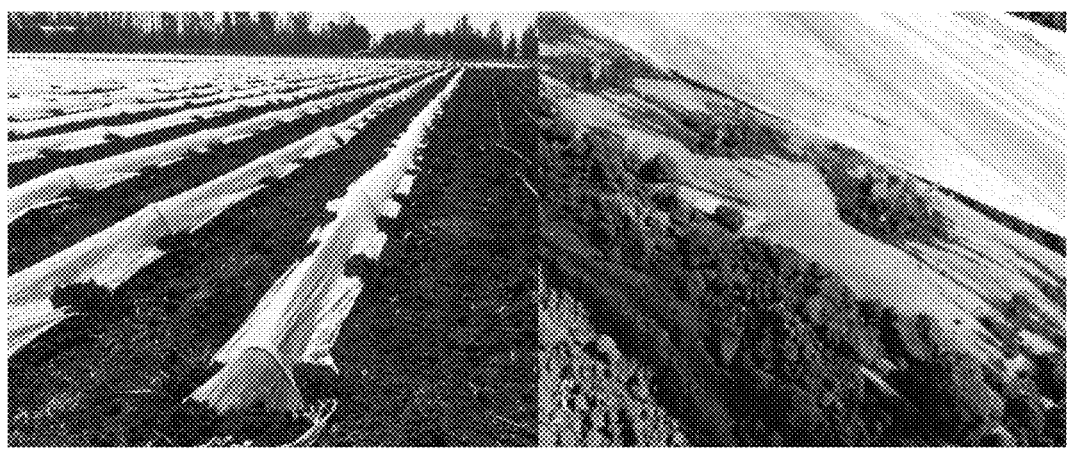
FIG. 1A illustrates an exemplary tomato field experiment where the transplanted plantlets are covered with polypropylene covering.
FIG. 1B illustrates field plot array for the experiment, showing fertilization conditions in culture lines, and plots along these lines, separated according to the type of bacterial treatment.
Figure 1:
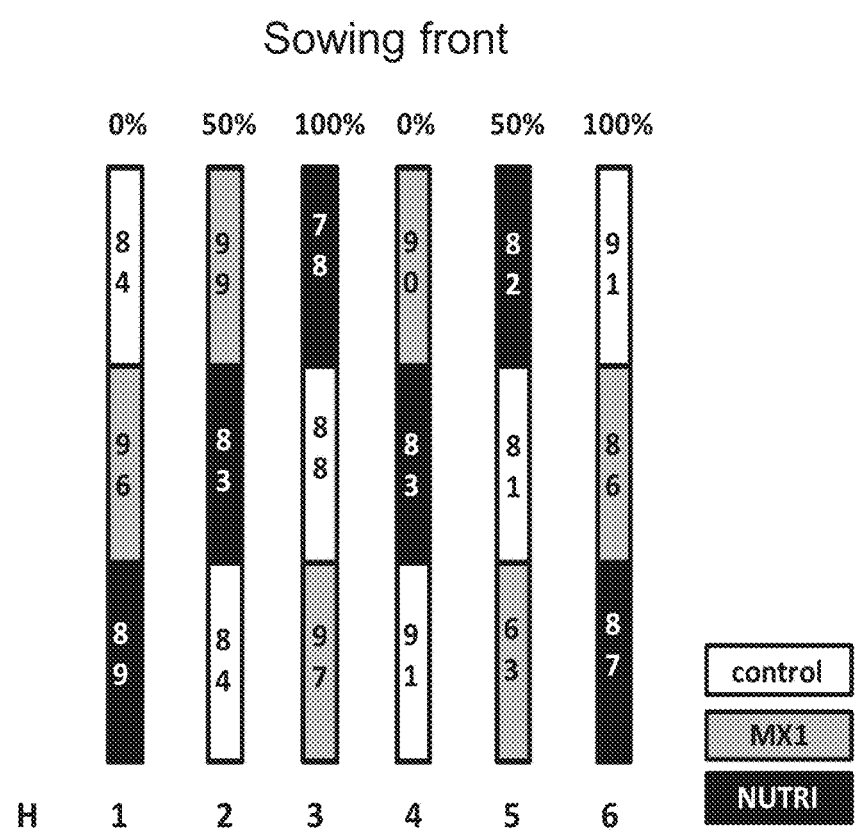

Before the disclosed methods and materials are described, it is to be understood that the aspects described herein are not limited to specific embodiments, methods, apparati, or configurations, and as such can, of course, vary. It is also to be understood that the terminology used herein is for the purpose of describing particular aspects only and, unless specifically defined herein, is not intended to be limiting.

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used in the specification and the appended claims, the singular forms "a," "an" and "the" include plural referents unless the context clearly dictates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein the term "combining" includes adding one or more items to a reaction mixture.

As used herein, "improved" or "Improving" should be taken broadly to encompass improvement of a characteristic of a plant, which may already exist in a plant or plants prior to application of the invention, or the presence of a characteristic which did not exist in a plant or plants prior to application of the invention. By way of example, "improved" growth should be taken to include growth of a plant where the plant was previously known to grow slowly, to a lesser extent, or not at all under the relevant conditions.

All percentages, ratios and proportions herein are by weight, unless otherwise specified. A weight percent (weight %, also as wt %) of a component, unless specifically stated to the contrary, is based on the total weight of the composition in which the component is included (e.g., on the total amount of the mixture).

In view of the present disclosure, the methods described herein can be configured by the person of ordinary skill in the art to meet the desired need. In general, the disclosed methods provide improvements in inoculation methods that ensure the presence of beneficial microorganisms in the rhizosphere of tomato and potato plants, and provide improved growth and pest resistance in these plants. Another substantial advantage of the methods of the disclosure is that tomato plants treated with methods of the disclosure require less added fertilizer. Such treated tomato plants show improved growth and/or yield as compared to the untreated plants when fertilization is lower than the normal agronomic standard. For example, when fertilization is 50% of standard values, tomato plants treated with the methods of the disclosure showed at least 25% increased vegetative growth (e.g., plants reached greater height and/or diameter than non-treated plants) and weight and the number of fruits increased by at least 30% (as compared to non-treated plants). On the other hand, potato plants treated with the methods of the disclosure showed an increased proportion of the weight yield of larger caliber tubers, when fertilization was 50% or lower than the agronomic standard values. Further, the methods of the disclosure allow for improved resistance to fungal attack. For example, tomato plants treated by methods of the disclosure showed at least 40% less susceptibility to attack by indigenous fungi and a 400% higher weight yield than control plants when no fungicide treatment was applied.

The methods of the disclosure employ plant cultivation compositions comprising a mixture of bacteria species in a suspension medium. Typically, the plant cultivation compositions and methods comprise diverse and environmentally adaptable plant-associated bacteria belonging to *Burkholderia* genus and/or *Azospirillum* genus. In one embodiment, the bacterial species mixture comprises *Burkholderia phymatum* and *Azospirillum brasilense* species. In another embodiment, the bacterial species comprises *Burkholderia phytofirmans*. In yet another embodiment, the bacterial species comprises *Burkholderia phymatum*. In another embodiment, the bacterial species mixture comprises *Burkholderia phytofirmans*, *Burkholderia phymatum*, and *Azospirillum brasilense* species. In another embodiment, the bacterial species mixture comprises two species selected from the group consisting of: *Burkholderia phytofirmans*, *Burkholderia phymatum*, and *Azospirillum brasilense*. In certain embodiments, the compositions of the disclosure comprise one bacterium species selected from *Burkholderia phytofirmans*, *Burkholderia phymatum*, and *Azospirillum brasilense*, and a suspension medium.

In some embodiments, *Burkholderia phytofirmans* is PsJN strain. *Burkholderia phytofirmans* PsJN is able to produce positive effects in horticultural crops, such as tomato and potato. It has been reported that this bacterium stimulates growth of inoculated plants and induces physiological changes enhancing their adaptation to environmental stresses. In addition, plants inoculated with strain PsJN present longer root systems, more secondary roots and root hairs; stronger stems and more lignin deposits on vascular bundles. Also, inoculated plants present high amounts of phenolic compounds and chlorophyll content, high cytokinin levels and a high phenylalanine ammonia lyase levels. Strain PsJN also enhances resistance to low levels of pathogens. See Poupin et al. (2013) *PLoS One*, 8(7): e69435.

*B. phymatum* strains have been shown to be able to fix nitrogen within root tissue (Moulin et al., (2014) "Complete Genome sequence of *Burkholderia phymatum* STM815(T), a broad host range and efficient nitrogen-fixing symbiont of *Mimosa* species. Stand Genomic Sci. 9(3):763-74). In some embodiments, *Burkholderia phymatum* is STM815 strain. This strain was originally isolated from *Machaerium lunatum* in French Guiana (Vandamme et al. (2002) *Syst. Appl. Microbiol.* 25: 507-512.)

*A. brasilense* strains have also been characterized as nitrogen fixers, but they exert this function as free-living component of rhizosphere soil microbiota (Ravikumar et al., (2012) "Population dynamics of free living, nitrogen fixing bacteria *Azospirillum* in Manakkudi mangrove ecosystem", India. J Environ Biol. 33(3):597-602). In some embodiments, *Azospirillum brasilense* is Sp7 or Sp7-S strain. These strains were described by Katupitiya et al. (1995) *App/ Environ Microbiol.* 61(5): 1987-95. In certain embodiment, *Azospirillum brasilense* is Sp7.

The bacterial species mixture of the disclosure further comprises *Bacillus amyloliquefaciens*. In some embodiments, *Bacillus amyloliquefaciens* is present as strain IN937a. In other embodiments, the bacterial species mixture of the disclosure further comprises *Bacillus subtilis*. In some other embodiments, *Bacillus subtilis* is present as strain GB03.

The bacterial species of the disclosure may be isolated from a source material (for example, the material in which they naturally reside) by any one of a number of standard techniques which will be readily known to skilled persons. For example and without limitation, these techniques in general employ processes by which a solid or liquid culture of a single species can be obtained in a substantially pure form, usually by physical separation on the surface of a solid microbial growth medium or by volumetric dilutive isolation into a liquid microbial growth medium. These processes may include isolation from dry material, liquid suspension, slurries or homogenates in which the material is spread in a thin layer over an appropriate solid gel growth medium, or serial dilutions of the material made into a sterile medium and inoculated into liquid or solid culture media. While not essential, the material containing the bacterial species may be pre-treated prior to the isolation process in order to either multiply all bacteria in the material by, e.g. enriching the material with microbial nutrients (for example, nitrates, sugars, or vegetable, microbial or animal extracts).

Typically, the plant cultivation compositions comprise bacterium species as described above in spore form or any other form capable of forming colonies. Each bacterial species may be independently present in a concentration between about $10^3$ to about $10^{12}$ Colony Forming Units (CFU) per mL of the suspension medium. In some embodiments, each bacteria species is present in a concentration between about $10^4$ to about $10^{12}$ CFU/mL, or about $10^5$ to about $10^{12}$ CFU/mL, or about $10^6$ to about $10^{12}$ CFU/mL, or about $10^7$ to about $10^{12}$ CFU/mL, or about $10^8$ to about $10^{12}$ CFU/mL, or about $10^9$ to about $10^{12}$ CFU/mL, or about $10^{10}$ to about $10^{12}$ CFU/mL, or about $10^4$ to about $10^{11}$ CFU/mL, or about $10^4$ to about $10^{10}$ CFU/mL, or about $10^6$ to about $10^{10}$ CFU/mL, or about $10^8$ to about $10^{10}$ CFU/mL, or about $10^9$ to about $10^{11}$ CFU/mL, or about $10^8$ to about $10^{10}$ CFU/mL of the suspension medium. In one embodiment, each bacteria species is present in a concentration of about $10^{10}$ CFU/mL of the suspension medium.

*Burkholderia phytofirmans*, *Burkholderia phymatum*, *Azospirillum brasilense* and/or *Bacillus subtilis* species are present in the bacterial species mixture in about an equal ratio (based on their respective CFU/mL concentration). For example, each of *Burkholderia phytofirmans*, *Burkholderia phymatum*, and *Azospirillum brasilense* bacterial species is present in about 1:1:1 ratio, or each of *Burkholderia phytofirmans*, *Burkholderia phymatum*, *Azospirillum brasilense*, and *Bacillus subtilis* bacterial species is present in about 1:1:1:1 ratio. In some other embodiments, the ratio of *Burkholderia phytofirmans*, *Burkholderia phymatum*, and *Azospirillum brasilense* species in the bacterial mixture is between about 2:1:1 to about 1:1:2, or between about 2:2:1 to about 1:2:2, or between about 1:2:1 to about 1:2:2, or between about 1:2:1 to about 2:2:1.

In some embodiments, each bacterial species independently makes up at least 10% of the bacterial species mixture (based on the total CFU/mL concentration). For example, in certain embodiments, each bacterial species independently makes up at least about 10% of the bacterial species mixture, or at least about 15%, or at least about 20%, or at least about 23%, or at least about 25%, or at least about 27%, or at least about 30%, or at least about 31%, or at least about 32%, or at least about 33%, or at least about 35%, or at least about 40%, of the bacterial species mixture. In some other embodiments, each bacterial species independently makes from about 10% to about 50% of the bacterial species mixture. In some other embodiments, each bacterial species independently makes from about 20% to about 50%, or form about 20% to about 40%, or form about 30% to about 40%, or form about 30% to about 35% of the bacterial species mixture.

The suspension medium used in the plant cultivation compositions of the disclosure may be media conventionally used in the art. Representative examples of suspension media include, but are not limited to, phosphate buffers, low-molecular-weight phosphate buffers, HEPES (4-(2-hydroxyethyl)-1-piperazineethanesulfonic acid) buffers, and sulfate buffers. In one embodiment, the suspension medium comprises one of more phosphate or sulfate buffers. In one embodiment, the suspension medium comprises one of more $NaH_2PO_4$, $K_2HPO_4$, $MgSO_4$, $ZnSO_4$, $FeSO_4$, and $Na_2SO_4$. In one embodiment, the suspension medium comprises one of more $NaH_2PO_4$, $K_2HPO_4$, and $MgSO_4$. The pH of the suspension medium may be in a range of from pH 4 to pH 11, or from pH 6 to pH 10.

The suspension medium may be amended or enriched with additional compounds or components. For example, nutrients (for example amino acid-rich extracts such as peptone, soytone, casaminoacids, or yeast extract; organic and inorganic minerals such as phosphorus, nitrogenous salts, ammonia, potassium; micronutrients such as cobalt and magnesium; and sugars), vitamins, growth promoters (e.g., auxins, gibberellins, cytokinins, and the like), biostimulants, and other substrates may be used.

In one embodiment, the plant cultivation compositions of the disclosure further comprise bacteria growth-promoting substrate. Growth-promoting substrate includes any medium which is suitable to support growth of a plant. By way of example and without limitation, the growth-promoting substrate includes one or more of soil (e.g., native or commercial), peat, turf, moss, perlite, potting mixes, bark, vermiculite, hydroponic solutions alone and applied to solid plant support systems, and tissue culture gels. It should be appreciated that the growth-promoting substrate may be used alone or in combination with one or more other media. It may also be used with or without the addition of exogenous nutrients and physical support systems for roots and foliage.

In one embodiment, the growth-promoting substrate is a naturally occurring medium such as soil, sand, mud, clay, humus, regolith, or rock. In another embodiment, the growth-promoting substrate is artificial. Such an artificial growth-promoting substrate may be constructed to mimic the conditions of a naturally occurring medium, however, this is not necessary. Artificial growth-promoting substrate can be made from one or more of any number and combination of materials including sand, minerals, glass, rock, water, metals, salts, and nutrients. In one embodiment, the growth-promoting substrate is sterile. In another embodiment, the growth-promoting substrate is not sterile.

In certain embodiments, the plant cultivation composition compromise from about 75 to about 99.99 weight % of bacteria growth-promoting substrate based on the total weight of the plant cultivation composition. In certain embodiments, the bacteria growth-promoting substrate is present from about 80 to about 99.99 weight %, or about 85 to about 99.99 weight %, or about 90 to about 99.99 weight %, or about 95 to about 99.99 weight %, or about 95 to about 99.9 weight %, or about 95 to about 99 weight %, or about 90 to about 99 weight %. In certain other embodiments, the growth-promoting substrate is present in about 99 weight % of the plant cultivation composition.

The plant cultivation compositions of the disclosure are used in methods for improving plant's resistance to fungal infection and in methods for promoting growth of plants. Thus, in one aspect, the disclosure provides methods for improving resistance of potato or tomato to indigenous fungi. In one embodiment, the fungi species is *Phytophtora infestans*. Such method comprises applying an effective amount of a plant cultivation composition of the disclosure to tomato seed or plantlet beds or to the surface of potato tuber-seed. In some embodiments, the plant cultivation composition is applied to the seed beds after planting or seeding. For example, the plants are first planted or sown into seed beds, followed by application of the plant cultivation composition. The application may be immediate or at a later time, after the plants are allowed to grow. In one embodiment, applying the plant cultivation composition is immediate. In another embodiment, applying the plant cultivation composition is one or more times between seeding and emerging. In some embodiments, application is repeated one or more times. The plant cultivation composition may be applied to the seed bed or the surface of tuber-seed using any appropriate techniques known in the art. For example, in one embodiment, the plant cultivation composition is applied by irrigation, spraying, or dusting.

Methods of the disclosure also include improving resistance of potato or tomato to indigenous fungi comprising applying an effective amount of a plant cultivation composition of the disclosure to tomato seed or plantlet or potato tuber to obtain treated seed or tuber, and sowing the treated seed or tuber. For example, seed or tuber may be coated with the plant cultivation composition by briefly immersing the seed or tuber into the plant cultivation composition. In one embodiment, the plant cultivation composition consists essentially of the bacterial species mixture of the disclosure, and the suspension medium. In one embodiment, the plant cultivation composition is additionally applied one or more times between seeding and emerging. The plant cultivation composition may be applied to the seed bed using any appropriate techniques known in the art. For example, in one embodiment, the plant cultivation composition is applied by irrigation, spraying, or dusting.

The methods of disclosure produce plants that have improved resistance to indigenous fungi compared to plants produced by conventional methods. For example, plants produced by methods of the disclosure are at least about 4 times more resistant to fungal infection compared to plants produced by conventional methods in the absence of fungicide treatment. In some embodiments, the plants treated with about 50% of standard fungicide treatment reach the same resistance level compared to plants that receive a full fungicide treatment (i.e., treated with a 100% fungicide). In other embodiments, the plants treated with about 40%, or about 30%, or about 25%, or about 55%, or about 60%, or about 70%, or about 75% of standard fungicide treatment reach the same resistance level compared to plants that received the full fungicide treatment.

In another aspect, the disclosure provides methods for promoting potato or tomato growth. As used herein, the term "promoting growth" should be taken broadly to encompass improvement in vegetative growth and/or height, weight and/or the number of fruits, resistance to weather elements, high survival, and decreased use of additional fertilizer. Such methods comprise applying an effective amount of a plant cultivation composition of the disclosure to tomato seed/plantlet beds or potato tubers. In some embodiments, the plant cultivation composition is applied to the seed beds after planting or seeding. For example, the plants are first planted or sown into seed beds, followed by application of the plant cultivation composition. The application may be immediate or at a later time, after the plants are allowed to grow. In one embodiment, applying the plant cultivation composition is immediate. In another embodiment, applying the plant cultivation composition is one or more times between seeding and emerging. In some embodiments, application is repeated one or more times. The plant cultivation composition may be applied to the seed bed using any appropriate techniques known in the art. For example, in one embodiment, the plant cultivation composition is applied by irrigation, spraying, or dusting. In some embodiments, one or more of vitamins, growth promoters, and biostimulants may also be applied.

Methods of the disclosure also include promoting potato or tomato growth comprising applying an effective amount of a plant cultivation composition of the disclosure to tomato seed/plantlet or potato tuber to obtain treated seed or tuber, and sowing the treated seed or tuber. For example, seed or tuber may be coated with the plant cultivation composition by briefly immersing the seed or tuber into the composition. In one embodiment, the plant cultivation composition consists essentially of the bacterial species mixture of the disclosure, and the suspension medium. In one embodiment, the plant cultivation composition is additionally applied one or more times between seeding and emerging. The plant cultivation composition may be applied to the seed bed using any appropriate techniques known in the art. For example, in one embodiment, the plant cultivation composition is applied by irrigation, spraying, or dusting. One or more of vitamins, growth promoters, and biostimulants may also be applied during sowing.

The methods of disclosure produce plants that require less additional fertilizer that plants produced by conventional methods. For example, use of additional fertilizer by tomato plants produced by methods of the disclosure is decreased by about 50% compared to plants produced by conventional methods. In some embodiments, the plants produced by the methods of the disclosure use at least 20% less, or at least 25% less, or at least 30% less, or at least 35% less, or at least 40% less, or at least 45% less fertilizer.

EXAMPLES

The methods of the disclosure are illustrated further by the following examples, which are not to be construed as limiting the disclosure in scope or spirit to the specific procedures and compounds described in them. In all cases, unless otherwise specified, the column chromatography is performed using a silica gel solid phase.

Example 1

*Burkholderia phytofirmans* strain PsJN (obtained from Dr. Angela Sessitsch), *Burkholderia phymatum* strain STM815 (obtained from DSMZ culture collection), and *Azospirillum brasilense* strain Sp7 (obtained from DSMZ culture collection) were separately grown in standard Luria Bertani (LB) broth (NaCl 0.5 grams/Liter (g/L), yeast extract 0.5 g/L, and peptone 1 g/L) for 48 hours. The cells were then harvested by centrifugation. The bacterial precipitate is washed with the selected suspension buffer, centrifuged again, and finally re-suspended in buffer to the final stock concentration of $1 \times 10^{10}$ CFU/mL of suspension. Suspension buffer is a phosphate buffer ($NaH_2PO_4$ 50 milimolar (mM), $K_2HPO_4$ 10 mM), a sulfate buffer ($MgSO_4$ 10 mM), or a combination of phosphate and sulfate buffer (1:1).

*Burkholderia phytofirmans* PsJN stock, *Burkholderia phymatum* STM815, and *Azospirillum brasilense* Sp7 stock were mixed to prepare the final plant cultivation solution having bacterial concentration of about $1 \times 10^{10}$ CFU for each strain/mL of suspension.

Mixtures of bacteria for treatments used in field experiments have been prepared as follows:
Control (also as uninoculated control) is a composition with no bacteria.
MX1 is a composition comprising *B. phytofirmans* PsJN.
NUTRIMIX (also as NUTRI) is a composition comprising a mixture of *B. phytofirmans* PsJN, *B. phymatum* STM815 and *A. brasilense* Sp7.
PROTEMIX (also as PROTE) is a composition comprising a mixture of *B. phytofirmans* PsJN, *A. brasilense* Sp7 and *B. subtilis* GB03.

Example 2

The plant cultivation solution of Example 1 is added to approximately 5 grams of seedbed substrate by irrigation of seedbeds. The turf-based substrate was mixed with a standard vitamin preparation for tomato seedlings according to commercial greenhouse production. The final concentration in the seedbed substrate is reached by adding one part (mL) of the plant cultivation solution to 10 parts (e.g., 10 grams) of seedbed substrate.

Tomato seeds were then sowed in the treated seedbeds. After plants emerged, no further treatment was performed. The subsequent culture of the plants followed standard agronomic procedure for growth of tomato. 4-5 week old plantlets were transplanted to soil plots at a density of approximately 25000 plants/Ha, subjected to a drip-irrigation system, and covered with polypropylene nets to protect them from chilling (FIG. 1A).

Figure 2:
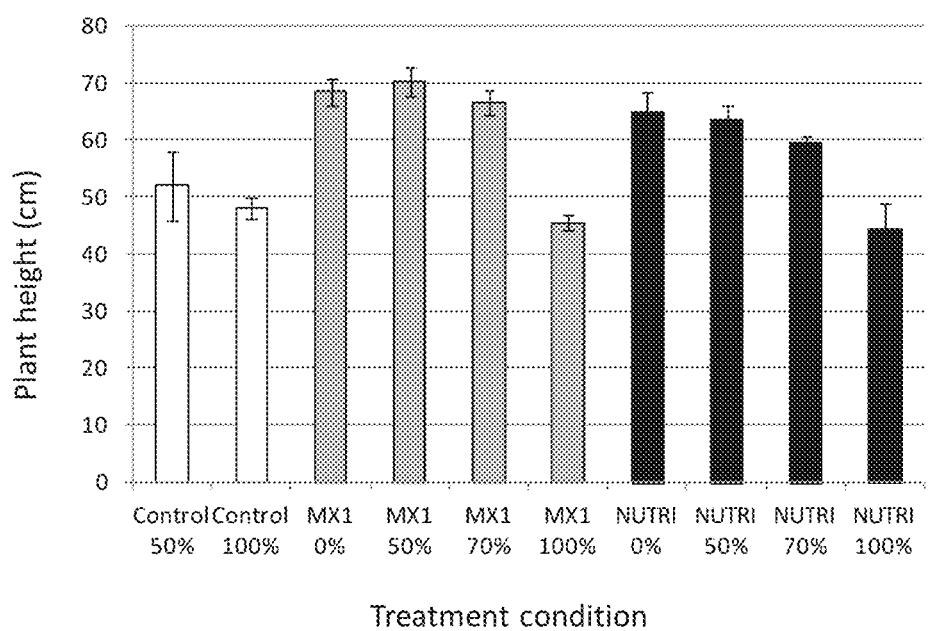
FIG. 2 shows vegetative growth by tomato plants grown in different field plots. Results represent plant height in a field experiment involving 1000 tomato plants, divided in field plots containing 100 plants per treatment condition. Data was registered 8 weeks after transplant to the field. Bars represent standard deviation values.

The results of the tomato field experiments have shown that vegetative growth of the plants is increased and/or accelerated in plants inoculated with MX1 and with NUTRIMIX when fertilization was equal or lower than 70% of the standard amount. In treatments at a 100% fertilization level, growth was similar to control plants (FIG. 2).

Figure 3:
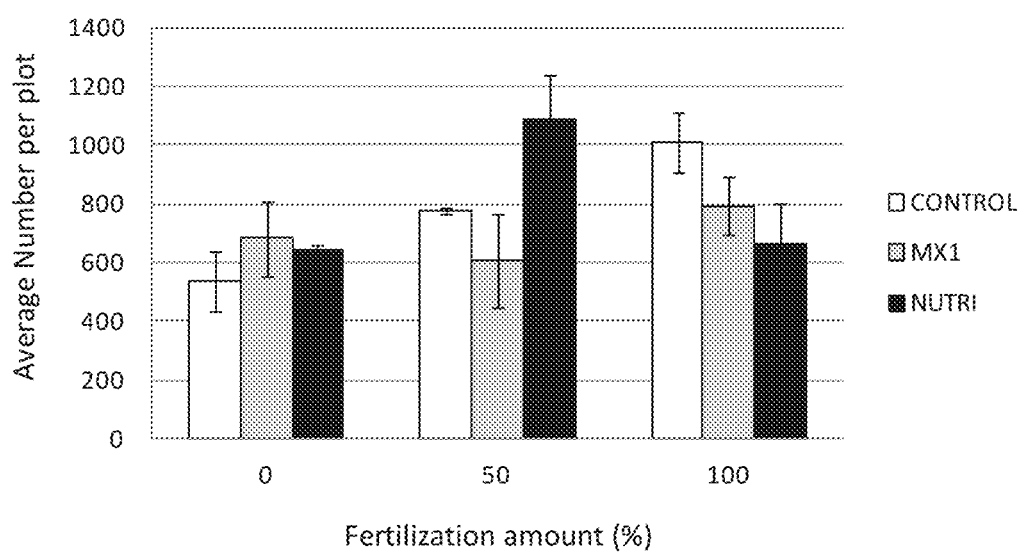
FIG. 3 shows comparison of the average fruit yield from different field plots. Data are collected from a field experiment using approximately 1620 tomato plants (180 plants per treatment) separated in randomized field plots. Results represent average values between replica plots for the total number of tomatoes collected in 4 consecutive harvesting dates.
Figure 4:
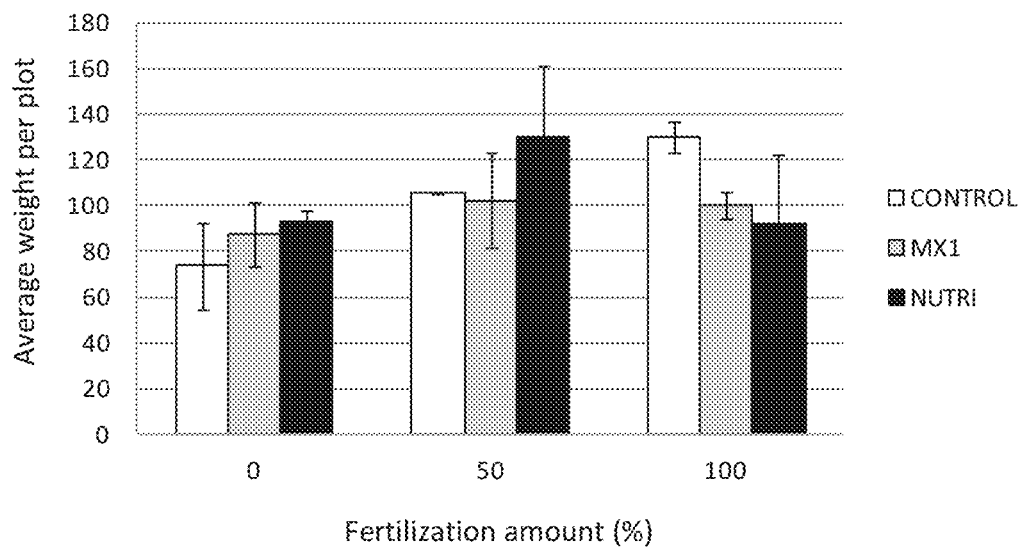
FIG. 4 shows average weight of total harvest from different field plots. Data are collected from a field experiment using approximately 3420 tomato plants (380 plants per treatment) separated in randomized field segments. Results are combined from 4 harvest periods.
Figure 5:
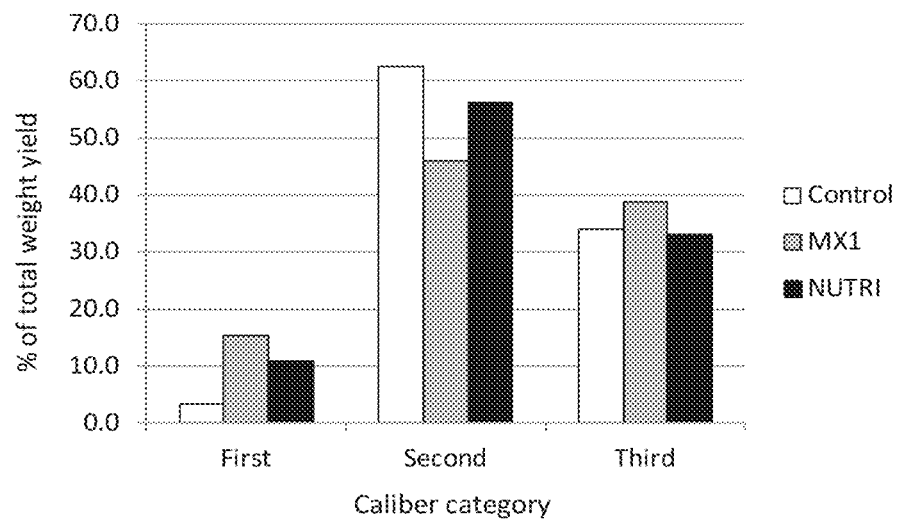
FIG. 5 shows tomato yield by caliber category where the total tomato weight from different plots was separated according to agricultural standards. Results show cumulative values from 4 consecutive harvest dates as percentages of total weight represented by each caliber within a specific inoculation condition.

Additional results are illustrated in FIGS. 3-5. In the 50% fertilization condition, total weight of tomato per field hectare was 47520 kg/Ha for control uninoculated plants, 46080 Kg/Ha for MX1 inoculated plants and 58567.5 Kg/Ha for NUTRIMIX inoculated plants. Therefore, a 23% increase in tomato weight yield was produced by inoculation of the PGPR-bacteria suspension, under this fertilization regime.

Example 3

Figure 6:
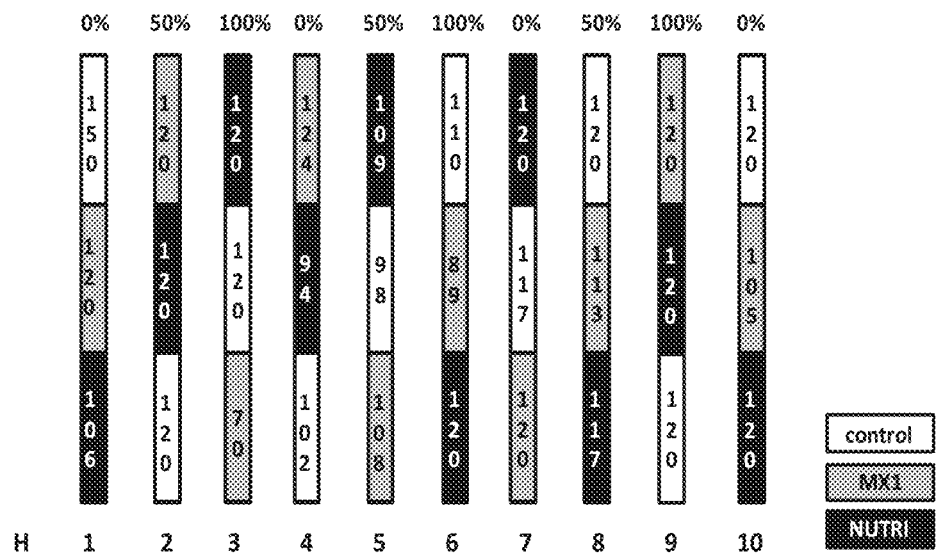
FIG. 6 illustrates the field plot array for an exemplary potato experiment, showing fertilization conditions in culture lines, and plots along these lines, separated according to the type of bacterial treatment.
Figure 7:
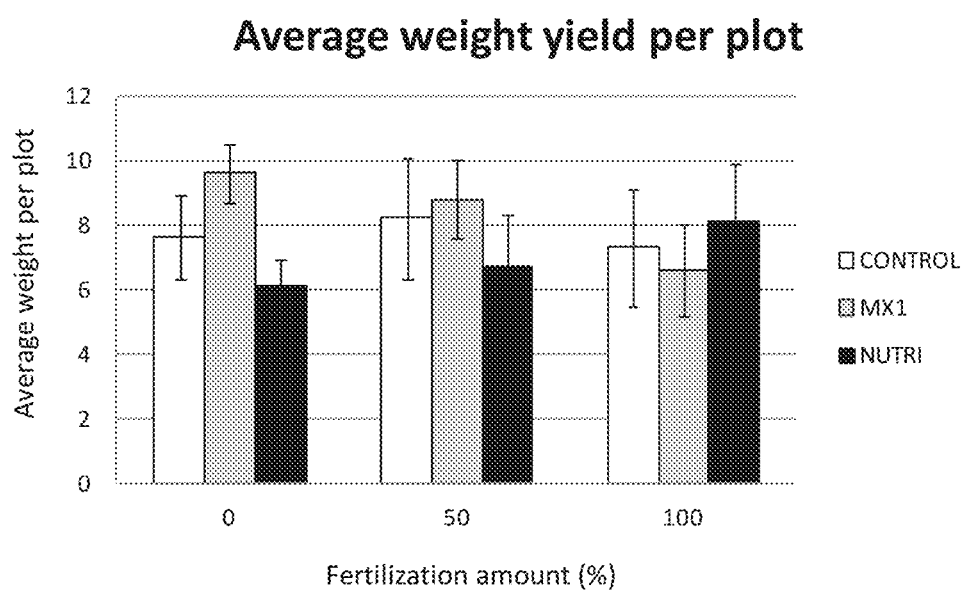
FIG. 7 shows the total weight yield of potato tubers for different treatments of Example 3.
Figure 8:
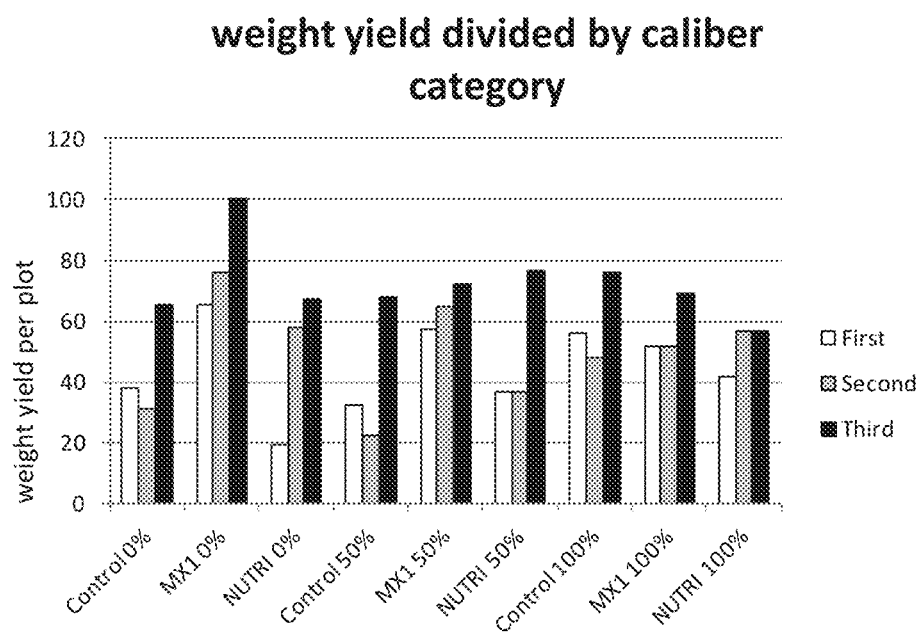
FIG. 8 shows the potato yield by caliber category where the total potato weight from different plots was separated according to agricultural standards. Results show the percentage of total weight represented by each caliber within a specific inoculation condition.

Potato tuber seeds were briefly immersed in the plant cultivation solution of Example 1. Potato tuber-seeds were inoculated by spraying or by immersion in diluted suspension solution, before direct sowing in field plots. The treated tubers were then sowed in the field as illustrated in FIG. 6. The results are shown in FIGS. 7 and 8.

Example 4

Plants cultivated as described in Example 2 and 3 were cultured using different fungicide treatment regimes in order to explore their susceptibility to infection by indigenous fungi, and the potential effect of these organisms on crop yield. To explore susceptibility in a controlled homogeneous environment, leaves were excised and collected from field plants to assay fungal growth in the laboratory. Samples were also collected to assay susceptibility to the phytopathogenic fungus *Phytophtora infestans*.

Figure 9:
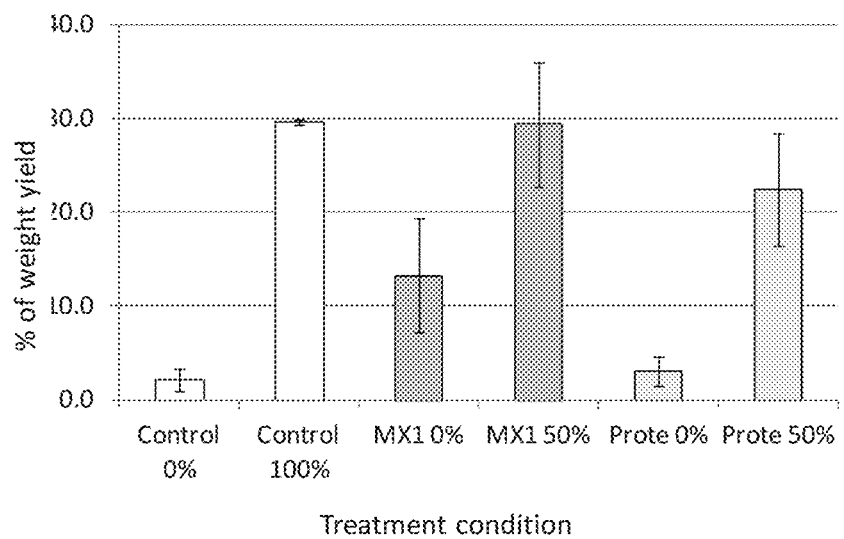
FIG. 9 shows the results of the fungal infection assay. Results of tomato weight yield were registered after 4 months and represent percentage of total yield as an average of 3 harvesting dates.

In a separate field area, 498 tomato plants that were grown in covered field plots, to increase humidity, and divided according to inoculum type (CONTROL-uninoculated; MX1-inoculated; or PROTEMIX-inoculated). The plants were treated with fungicide at different levels (i.e., 100%; 50% or 0%). Results of tomato weight yield were registered after 4 months and represent percentage of total yield as an average of 3 harvesting dates, and are shown in FIG. 9. Sign of fungal attack were present in every plant in the covered field, but appeared to be more severe for plants without fungicide treatment.

Figure 10:
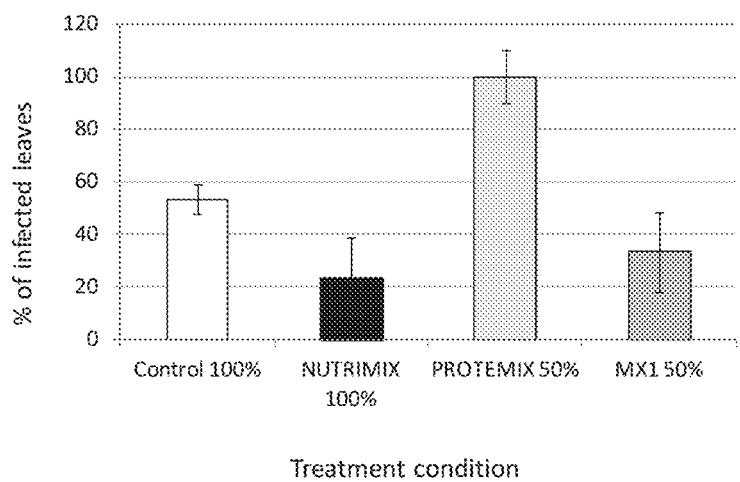
FIG. 10 shows the susceptibility of plants grown in the field to fungal attack by detaching leaves from plants belonging to each treatment condition, and exposing them to high humidity at 30° C. in a controlled culture chamber. Attack by indigenous fungi, colonizing the surface of leaves was monitored for 3 weeks, during which, the appearance of invasive fungal mycelium was confirmed by microscopy. Results are expressed as average percentage of leaves affected by fungal infection per treatment.

Plants grown in the field were also tested for susceptibility to fungal attack by detaching leaves from plants belonging to each treatment condition, and exposing them to high humidity at 30° C. in a controlled culture chamber. Attack by indigenous fungi, colonizing the surface of leaves was monitored for 3 weeks, during which, the appearance of invasive fungal mycelium was confirmed by microscopy. Results are expressed as average percentage of leaves affected by fungal infection per treatment and shown in FIG. 10.

A set of leaves was also inoculated with the phytopathogenic fungus *Phytophtora infestans*; however, development of *P. infestans* was not observed on tomato leaves. Specifically, randomly selected plants (n=10) were inoculated with *P. infestans* for every treatment condition. No specific signs of *P. infestans* infection were observed 2 weeks after inoculation, and *P. infestans* DNA could not be detected in tissue samples obtained from the inoculated plants after this period of incubation.

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

What is claimed:

1. A plant cultivation composition, comprising a) a plant growth-promoting rhizobacteria species mixture comprising *Burkholderia phytofirmans* PsJN strain, *Burkholderia phymatum* STM815 strain and *Azospirillum brasilense* Sp7 strain, wherein each said strain independently makes up from about 30% to about 40% of the rhizobacteria species mixture based on the total concentration of the rhizobacteria mixture; and b) a suspension medium.

2. The plant cultivation composition of claim 1, wherein each of the strains is independently present in a concentration between about $10^3$ to about $10^{12}$ Colony Forming Units (CFU) per mL of the suspension medium.

3. The plant cultivation composition of claim 1, wherein the strains are present in about 1:1:1 ratio.

4. The plant cultivation composition of claim 1, wherein the species mixture further comprises *Bacillus subtilis*.

5. The plant cultivation composition of claim 1, wherein the suspension medium comprises one of more phosphate or sulfate buffers.

6. The plant cultivation composition of claim 1, further comprising growth-promoting substrate.

7. A method for improving resistance to fungal infection, comprising applying an effective amount of the plant cultivation composition of claim 1 to tomato or potato seed beds.

8. The method of claim 7, wherein the applying is repeated one or more times.

9. A method for improving resistance to fungal infection, comprising applying an effective amount of the plant cultivation composition of claim 1 to tomato seed or plantlet or potato tuber to obtain treated seed, plantlet, or tuber, and sowing the treated seed or tuber.

10. The method of claim 9, further comprising applying one or more of vitamins, growth promoters, and biostimulants during sowing.

11. The method of claim 9, wherein the plant cultivation composition is applied one or more times after sowing.

12. A method for promoting tomato or potato growth, comprising applying an effective amount of the plant cultivation composition of claim 1 to tomato or potato seed beds.

13. The method of claim 12, wherein the applying is repeated one or more times.

14. The method of claim 12, wherein use of fertilizer is decreased by at least about 25%.

15. A method for promoting tomato or potato growth, comprising applying an effective amount of the plant cultivation composition of claim 1 to tomato seed or plantlet or potato tuber to obtain treated seed, plantlet, or tuber, and sowing the treated seed or tuber.

16. The method of claim 15, wherein use of fertilizer is decreased by at least about 25%.

* * * * *